(12) United States Patent
Xing et al.

(10) Patent No.: US 11,456,144 B2
(45) Date of Patent: Sep. 27, 2022

(54) ARC-SHAPED MULTI-FOCAL POINT FIXED ANODE GATE CONTROLLED RAY SOURCE

(71) Applicants: Jinhui Xing, Beijing (CN); Zhili Cui, Beijing (CN); Jian Gao, Beijing (CN); Hongguang Cao, Beijing (CN)

(72) Inventors: Jinhui Xing, Beijing (CN); Zhili Cui, Beijing (CN); Jian Gao, Beijing (CN); Hongguang Cao, Beijing (CN)

(73) Assignee: NANOVISION TECHNOLOGY (BEIJING) CO., LTD, Beijing (CN)

( * ) Notice: Subject to any disclaimer, the term of this patent is extended or adjusted under 35 U.S.C. 154(b) by 0 days.

(21) Appl. No.: 16/910,069

(22) Filed: Jun. 24, 2020

(65) Prior Publication Data
US 2020/0321183 A1 Oct. 8, 2020

Related U.S. Application Data

(63) Continuation of application No. PCT/CN2018/123607, filed on Dec. 25, 2018.

(30) Foreign Application Priority Data

Dec. 25, 2017 (CN) .......................... 201711418215.5

(51) Int. Cl.
*H01J 35/04* (2006.01)
*H05G 1/70* (2006.01)
(Continued)

(52) U.S. Cl.
CPC .......... *H01J 35/045* (2013.01); *A61B 6/4007* (2013.01); *H05G 1/70* (2013.01); *H01J 35/025* (2013.01)

(58) Field of Classification Search
CPC ........ H01J 35/045; H01J 35/02; H01J 35/025; A61B 6/4007; H05G 1/70
See application file for complete search history.

(56) References Cited

U.S. PATENT DOCUMENTS 3,878,394 A * 4/1975 Golden ................. H01J 35/165
378/102
7,233,644 B1 6/2007 Bendahan et al.
(Continued)

FOREIGN PATENT DOCUMENTS

| CN | 105997127 A | * 10/2016 | |
| WO | 2018153382 A1 | 8/2018 | |
| WO | WO-2018153382 A1 | * 8/2018 | ........... A61B 6/4028 |

OTHER PUBLICATIONS

Extended European Search Report dated Sep. 24, 2021 for European Patent Application 18895942.3.

*Primary Examiner* — Chih-Cheng Kao
(74) *Attorney, Agent, or Firm* — George Guosheng Wang; Upstream Research and Patent LLC

(57) ABSTRACT

Provided is an arc-shaped multi-focal point fixed anode gate controlled ray source, comprising an arc-shaped ray source housing, a ray tube bracket, a plurality of fixed anode reflected ray tubes and a plurality of gate controlled switches, wherein the plurality of fixed anode reflected ray tubes are fixed on the arc-shaped ray source housing by means of the ray tube bracket, and the focal points of the plurality of fixed anode reflected ray tubes are distributed on the same distribution circle; and the plurality of gate controlled switches are correspondingly connected to the plurality of fixed anode reflected ray tubes. By splicing the plurality of arc-shaped multi-focal point fixed anode gate controlled ray sources into an integral ring stricture, the focal points of all the fixed anode reflected ray tubes therein can be distributed on, the same distribution circle.

9 Claims, 3 Drawing Sheets

(51) Int. Cl.
*A61B 6/00* (2006.01)
*H01J 35/02* (2006.01)

(56) References Cited

U.S. PATENT DOCUMENTS

| | | | |
|---|---|---|---|
| 2006/0274891 A1 | 12/2006 | Bhatt et al. | |
| 2008/0226033 A1* | 9/2008 | Schardt | H05G 1/70 |
| | | | 378/134 |
| 2012/0051510 A1* | 3/2012 | Ohta | A61B 6/542 |
| | | | 378/62 |
| 2012/0189094 A1* | 7/2012 | Neushul | A61B 6/4266 |
| | | | 378/19 |
| 2013/0003913 A1 | 1/2013 | Jeong et al. | |
| 2014/0247923 A1* | 9/2014 | Park | H01J 35/12 |
| | | | 378/138 |
| 2015/0078532 A1* | 3/2015 | Tang | H01J 35/14 |
| | | | 378/134 |

* cited by examiner

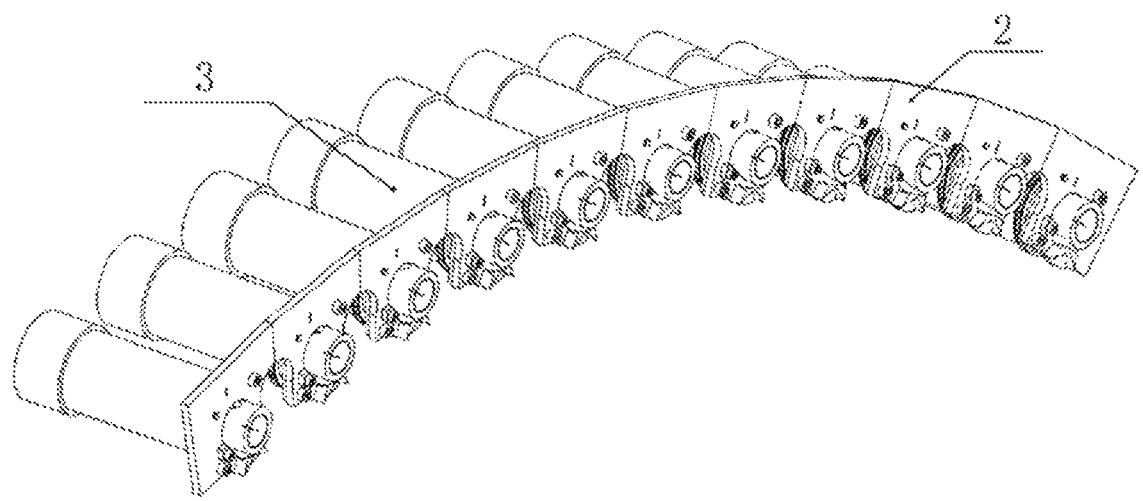
FIG. 2
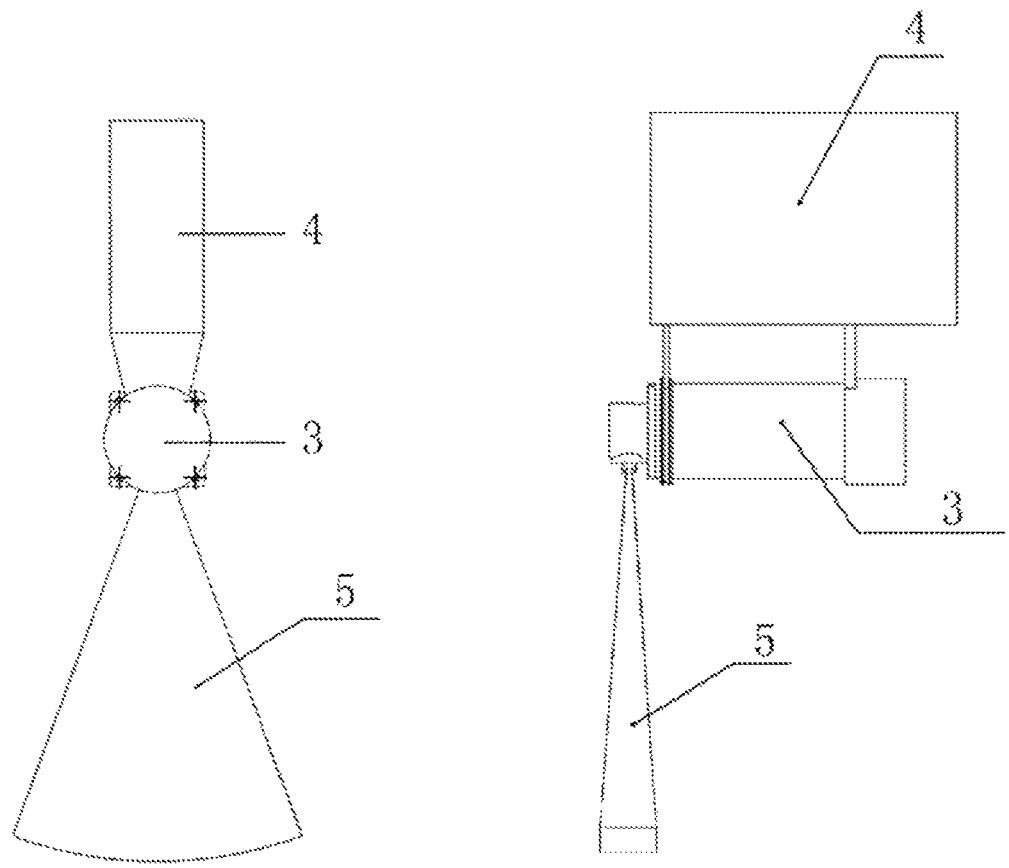
FIG. 3A
FIG. 3B

ARC-SHAPED MULTI-FOCAL POINT FIXED ANODE GATE CONTROLLED RAY SOURCE

BACKGROUND

Technical Field

The invention relates to an X ray source, in particular to an arc-shaped multi-focal point fixed anode gate controlled ray source.

Related Art

Static CT is a novel CT (Computed Tomography) technical solution, according to an overall structure of the static CT, a full circle of detectors and a full circle of ray sources are adopted, and through sequential raying of focal points of various ray sources on the circumference, a purpose of circular scanning like helical CT is achieved. The static CT has no need of rotating components in theory, and thus has no need of a bearing and a sliding ring, the structure is simple, the theoretical circular scanning speed is high, and the data transmission speed is high.

At present, in the field of static CT, there are two current mainstream ideas of the full circle of ray sources: 1. reflected raying is adopted, and an integral ring of fixed anodes is matched with a plurality of cathodes uniformly distributed circumferentially to form a circumferential multi-focal point annular ray source, but such anodes of the integral ring is difficult to manufacture because of large diameter; 2. transmission type raying is adopted, a ray source structure is modularized, a plurality of focal points are arranged in one module, and a plurality of ray source modules are distributed in a circumferential direction to realize an integral ring structure, but the ray strength of such structure is low, and thus, the structure is not suitable for practical detection.

Therefore, the X ray source further needs to be improved such that the X ray source can generate a ray of sufficient strength, and have a sufficient number of focal points distributed in the circumferential direction.

SUMMARY

The present invention aims to provide an arc-shaped multi-focal point fixed anode gate controlled ray source.

In order to achieve the object of the present invention, the present invention adopts the following technical solution.

According to a first aspect of an embodiment of the present invention, provided is an arc-shaped multi-focal point fixed anode gate controlled ray source, including an arc-shaped ray source housing, a ray tube bracket, a plurality of fixed anode reflected ray tubes and a plurality of gate controlled switches; where the plurality of fixed anode reflected ray tubes are fixed on the arc-shaped ray source housing through the ray tube bracket, and focal points of the fixed anode reflected ray tubes are distributed on a same distribution circle; and the plurality of gate controlled switches are correspondingly connected with the plurality of fixed anode reflected ray tubes.

Preferably, an included angle $\theta$ between an outer edge of a left side plate and an outer edge of a right side plate of the arc-shaped ray source housing equals to $360°/N$, and N is a positive integer.

Preferably, the ray tube bracket is an arc-shaped bracket, the ray tube bracket is fixed on an inner arc wall plate of the arc-shaped ray source housing, the plurality of fixed anode reflected ray tubes are fixed on the ray tube bracket, and the focal points of the plurality of fixed anode reflected ray tubes are uniformly distributed on the same distribution circle.

Preferably, the ray tube bracket is uniformly provided with a plurality of through holes, anode ends of the plurality of fixed anode reflected ray tubes extend out of the through holes of the ray tube bracket respectively, and the plurality of fixed anode reflected ray tubes are fixed on the ray tube bracket through flanges respectively.

Preferably, the inner arc wall plate and an outer arc wall plate of the arc-shaped ray source housing are respectively concentric to a distribution circle on which the focal points of the plurality of fixed anode reflected ray tubes are located; and extension lines of the left side plate and the right side plate of the arc-shaped ray source housing pass through the center of the distribution circle on which the focal points of the plurality of fixed anode reflected ray tubes are located.

Preferably, the focal points of the plurality of fixed anode reflected ray tubes are uniformly distributed in an angle range $\alpha$ relative to a same distribution circle, $360° \geq \alpha > 0°$, and $\alpha$ is smaller than or equal to $\theta$.

Preferably, when $\alpha = \theta$, in the n fixed anode reflected ray tubes arranged in the same arc-shaped ray source housing, an angle between two adjacent fixed anode reflected ray tubes is $\theta/n$, and the angle between the fixed anode reflected ray tubes on the leftmost side and the rightmost side and outer edges of adjacent side plates is $\theta/2n$.

Preferably, when $\alpha < \theta$, the angle between two adjacent fixed anode reflected ray tubes is $\alpha/n$.

Preferably, each fixed anode reflected ray tube is provided with an independent gate controlled switch; and the gate controlled switch is fixed to a tube body of the fixed anode reflected ray tube through a bracket, and an output end of the gate controlled switch is connected to a gate of the fixed anode reflected ray tube through a wire.

According to a second aspect of an embodiment of the present invention, provided is an X ray source, including a plurality of the arc-shaped multi-focal point fixed anode gate controlled ray sources, where the plurality of arc-shaped multi-focal point fixed anode gate controlled ray sources are assembled into an integral ring structure, and focal points of all the fixed anode reflected ray tubes in the arc-shaped multi-focal point fixed anode gate controlled ray sources are circumferentially distributed on a same distribution circle.

The arc-shaped multi-focal point fixed anode gate controlled ray source provided by the present invention includes the fixed anode reflected ray tubes, the gate controlled switches, the ray tube bracket and the arc-shaped ray source housing, where the anode ends of the fixed anode reflected ray tubes generate X ray beams by using a reflected fixed anode target, the plurality of fixed anode reflected ray tubes are fixed on the arc-shaped ray source housing through the ray tube bracket, and the plurality of fixed anode reflected ray tubes are uniformly distributed in a certain angle range relative to the distribution circle with a certain size. A plurality of arc-shaped ray source housing can be assembled into an integral ring structure, and thus, the focal points of all the fixed anode reflected ray tubes in the arc-shaped multi-focal point fixed anode gate controlled ray sources are distributed on the same distribution circle. In the arc-shaped multi-focal point fixed anode gate controlled ray source, the plurality of gate controlled switches are correspondingly connected with the plurality of fixed anode reflected ray tubes, the gate controlled switch can control on and off of circuits of the fixed anode reflected ray tubes, and thus, control on raying is realized. The arc-shaped multi-focal point fixed anode gate controlled ray source is simple in structure and lower in cost, and can generate a ray of sufficient strength, and meanwhile, a sufficient number of focal points can be distributed in the circumferential direction.

BRIEF DESCRIPTION OF THE DRAWINGS

FIG. 2 is a schematic diagram of connection between fixed anode reflected ray tubes and a ray tube bracket in FIG. 1, FIG. 3A is a front view of a connection structure of the fixed anode reflected ray tubes and gate controlled switches;

FIG. 3B is a side view of a connection structure of the fixed anode reflected ray tubes and the gate controlled switches.

DETAILED DESCRIPTION

The technical content of the invention are further described below with reference to the accompanying drawings and specific embodiments.

Figure 1:
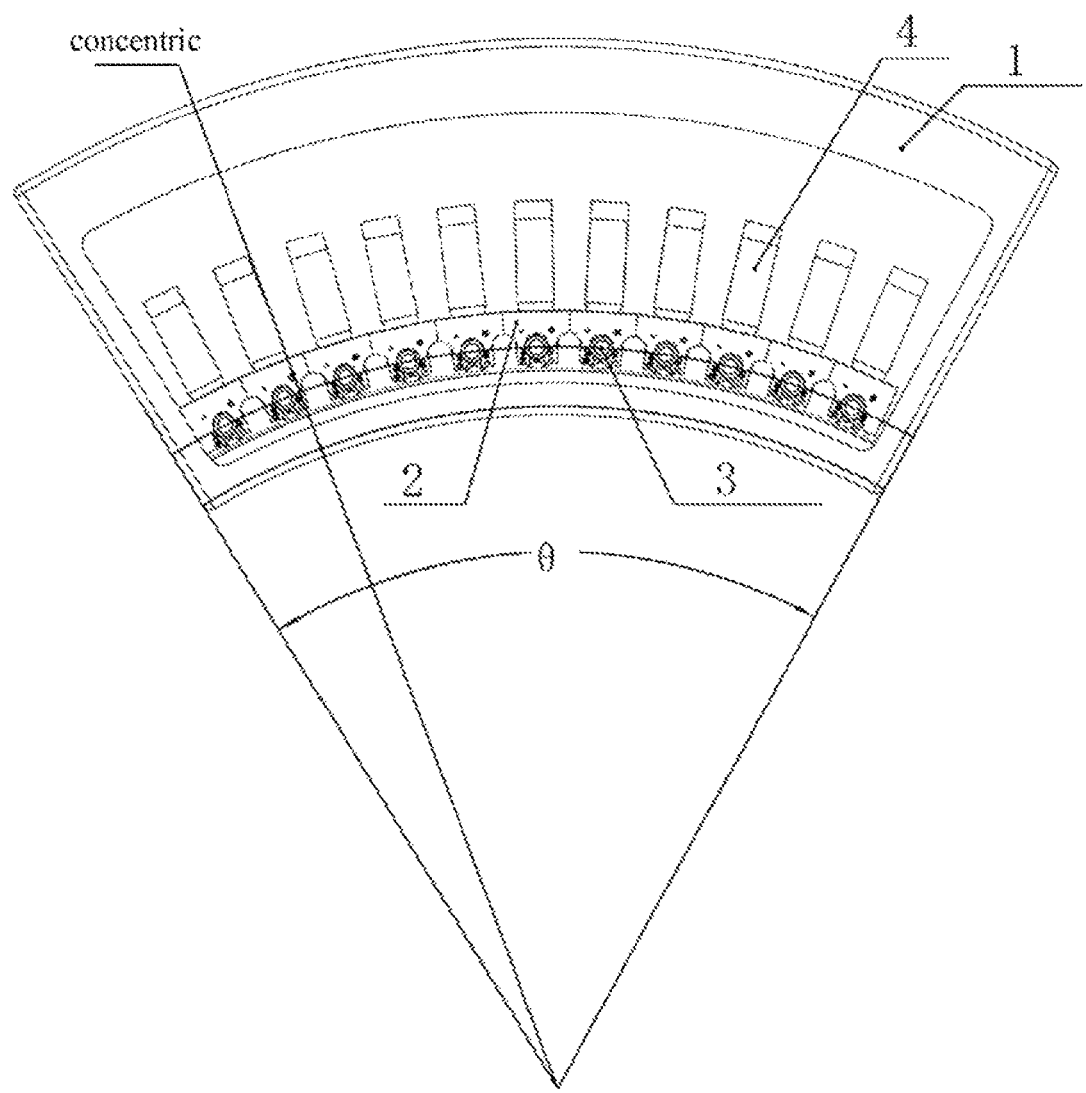
FIG. 1 is a schematic diagram of an overall structure of an arc-shaped multi-focal point fixed anode gate controlled ray source according to the present invention.

As shown in FIG. 1, an arc-shaped multi-focal point fixed anode gate controlled ray source provided by the present invention includes an arc-shaped ray source housing 1, a ray tube bracket 2, a plurality of fixed anode reflected ray tubes 3 and a plurality of gate controlled switches 4. The plurality of fixed anode reflected ray tubes 3 are fixed on the arc-shaped ray source housing 1 through the ray tube bracket 2, focal points of the plurality of fixed anode reflected ray tubes 3 are distributed on a same distribution circle, and preferably, the focal points of the plurality of fixed anode reflected ray tubes 3 are uniformly distributed in a certain angle range $\alpha$ (360°≥$\alpha$>0°) relative to the same distribution circle, and the plurality of gate controlled switches 4 are correspondingly connected with the plurality of fixed anode reflected ray tubes 3, and are used for controlling on and off of the plurality of fixed anode reflected ray tubes 3.

The specific structure of the arc-shaped multi-focal point fixed anode gate controlled ray source is described below with the orientation shown in FIG. 1 as an example.

Specifically, as shown in FIG. 1, the arc-shaped ray source housing 1 is a closed housing consisting of an inner arc wall plate, an outer arc wall plate, a left side plate, a right side plate, a front side plate and a rear side plate, and the ray tube bracket 2, the plurality of fixed anode ray tubes 3 and the plurality of gate switches 4 are all disposed inside the arc-shaped ray source housing 1. An included angle $\theta$ between an outer edge of a left side plate and an outer edge of a right side plate of the arc-shaped ray source housing 1 may be optionally selected in a range of 0° to 360°, $\theta$ is preferably 360°/N, and N is a positive integer, for example, $\theta$ is equal to 45°, 60°, 90°, 180° and the like. When $\theta$=360°/N and N is larger than 1, the N arc-shaped multi-focal point fixed anode gate controlled ray sources can form an integral ring structure by assembling the N arc-shaped ray source housings 1 around a circumference, so that the focal points of the plurality of fixed anode reflected ray tubes 3 can be distributed on a same distribution circle. It will be appreciated that when $\theta$=360°/N and N=1, the entire arc-shaped ray source housing will be a circular ring structure, and the left side plate and the right side plate do not exist theoretically.

As shown in FIG. 2, the ray tube bracket 2 is an arc-shaped bracket, the ray tube bracket 2 is fixed on the inner arc wall plate of the arc-shaped ray source housing 1 through connectors such as bolts, and the plurality of fixed anode reflected ray tubes 3 are fixed on the ray tube bracket 2.

The ray tube bracket 2 is uniformly provided with a plurality of through holes, anode ends of the plurality of fixed anode reflected ray tubes 3 extent out from the through holes of the ray tube bracket 2 respectively, and the fixed anode reflected ray tubes 3 are fixed on the ray tube bracket 2 through flanges respectively. In an actual structure, the focal points of the fixed anode reflected ray tubes 3 can be adjusted to the same circle by fine adjustment of fixed positions and angles of the fixed anode reflected ray tubes 3 on the ray tube bracket 2. Hereinafter, a circle passing through the focal points of the plurality of fixed anode reflected ray tubes 3 is referred to as a distribution circle of the plurality of fixed anode reflected ray tubes 3.

An inner end surface and an outer end surface of the arc-shaped ray source housing 1 are cambered surfaces, and the inner arc wall plate and the outer arc wall plate are concentric to the distribution circle of the plurality of fixed anode reflected ray tubes 3 respectively. Certainly, the inner arc wall plate and the outer arc wall plate may also be approximately concentric to the distribution circle of the plurality of fixed anode reflected ray tubes, but the inner arc wall plate and the outer arc wall plate are optimally concentric to the distribution circle of the plurality of fixed anode reflected ray tubes. A left end surface and a right end surface of the arc-shaped ray source housing 1 form an included angle $\theta$, and the extension lines of the left side plate and the right side plate optimally pass through the center of the distribution circle of the plurality of fixed anode reflected ray tubes 3.

The focal points of the plurality of fixed anode reflected ray tubes 3 are uniformly distributed in a certain angle range $\alpha$ relative to the distribution circle, and the angle range $\alpha$ is smaller than or equal to an angle $\theta$ between the outer edge of the left side plate and the outer edge of the right side plate of the arc-shaped ray source housing 1. In an actual structure, when the wall thickness of the left side plate and the wall thickness of the right side plate are small and the number of the fixed anode reflected ray tubes 3 arranged in one arc-shaped ray source housing 1 is small, $\alpha$ and $\theta$ are approximately equal to each other, preferably, in the n fixed anode reflected ray tubes 3 arranged in the same arc-shaped ray source housing 1, an angle between, two adjacent fixed anode reflected ray tubes 3 is $\theta/n$, and an angle between the fixed anode reflected ray tubes 3 on the leftmost side and the rightmost side and outer edges of adjacent side plates is $\theta/2n$. When the wall thickness of the left side plate and the wall thickness of the right side plate are large or the number of the fixed anode reflected ray tubes 3 arranged in one arc-shaped ray source housing 1 is large, $\alpha$ is smaller than $\theta$, the angle between two adjacent fixed anode reflected ray tubes 3 is $\alpha/n$, and the angle between the fixed anode reflected ray tubes 3 on the leftmost side and the rightmost side and the outer edges of the adjacent side plates may be greater than $\alpha/2n$, and may also be smaller than $\alpha/2n$.

The anode ends of the fixed anode reflected ray tubes 3 used in the present invention generate an X ray beam by using a reflected fixed anode target. Two ends of the fixed anode reflected ray tube 3 are an anode end and a cathode end respectively, and a gate is arranged close to the cathode in the fixed anode reflected ray tube 3. As shown in FIG. 3A and FIG. 3B, each fixed anode reflected ray tube 3 is provided with an independent gate controlled switch 4. The gate controlled switch 4 is fixed to a tube body of the fixed anode reflected ray tube 3 through a bracket, and an output end of the gate controlled switch 4 is connected to the gate of the fixed anode reflected ray tube 3 through a wire, so that on and off of the fixed anode reflected ray tube 3 are controlled, control on raying is realized, and an X ray beam 5 emitted after being reflected by the anode ends is as shown in FIG. 3A and FIG. 3B. Certainly, on and off of a plurality of adjacent fixed anode reflected ray tubes 3 may also be controlled by a same gate controlled switch 4. However, among the foregoing control modes, the fixed anode reflected ray tubes 3 and the gate switched switches 4 are preferably controlled in a one-to-one correspondence mode as shown in the drawings.

Figure 4:
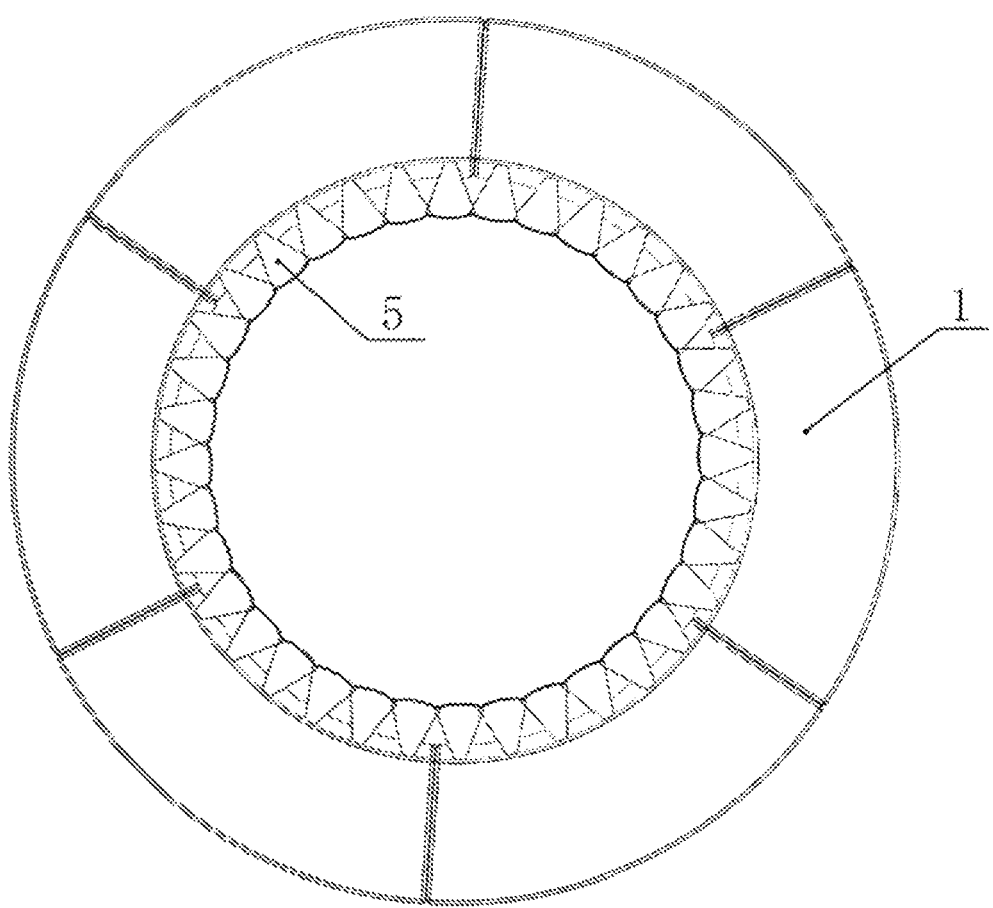
FIG. 4 is a schematic diagram of an overall ring structure consisting of a plurality of arc-shaped multi-focal point fixed anode gate controlled ray sources.

As shown in FIG. 4, the left side plates and the right side plates of N arc-shaped ray source housings 1 are connected end to end, such that the N arc-shaped multi-focal point fixed anode gate controlled ray sources are assembled into an 'integral ring structure', and thus, the focal points of the plurality of fixed anode reflected ray tubes 3 can be circumferentially distributed on the same distribution circle, and are uniformly distributed as much as possible. Through control on the gate controlled switches 4 in the integral ring structure, the fixed anode reflected ray tubes 3 sequentially emit X ray beams, and thus, sequential raying scanning in a 360° direction can be realized. In the integral ring structure, the X ray beam 5 emitted by each fixed anode reflected ray tube 3 irradiates to the center of an integral ring.

When the angle between two adjacent fixed anode reflected ray tubes 3 arranged in the same arc-shaped ray source housing 1 is θ/n and the angle between the fixed anode reflected ray tubes 3 on the leftmost side and the rightmost side and the outer edges of adjacent side plates is θ/2n, the N arc-shaped multi-focal point fixed anode gate controlled ray sources form an integral ring structure, such that the focal points of all the fixed anode reflected ray tubes 3 in the N arc-shaped multi-focal point fixed anode gate controlled ray sources are uniformly distributed on the distribution circle. When the angle between two adjacent fixed anode reflected ray tubes 3 arranged in the same arc-shaped ray source housing 1 is another value, in the integral ring structure consisting of the N arc-shaped multi-focal point fixed anode gate controlled ray sources, the focal points of all the fixed anode reflected ray tubes 3 in the N arc-shaped ray source housing 1 are distributed on the same distribution circle, and the focal points of the plurality of fixed anode reflected ray tubes 3 in each arc-shaped ray source housing 1 are uniformly distributed.

In conclusion, the arc-shaped multi-focal point fixed anode gate controlled ray source provided by the present invention includes the fixed anode reflected ray tubes, the gate controlled switches, the ray tube bracket and the arc-shaped ray source housing. The fixed anode reflected ray tubes can emit the X ray beams, the plurality of fixed anode reflected ray tubes can be fixed on the arc-shaped ray source housing through the ray tube bracket, and the plurality of fixed anode reflected ray tubes are uniformly distributed in a certain angle range relative to the distribution circle with a certain size. The plurality of arc-shaped ray source housings can be assembled into an integral ring structure, so that the focal points of all the fixed anode reflected ray tubes in the plurality of arc-shaped multi-focal point fixed anode gate controlled ray sources are distributed on the same distribution circle. In the arc-shaped multi-focal point fixed anode gate controlled ray source, the plurality of gate controlled switches and the plurality of fixed anode reflected ray tubes are connected correspondingly, and the gate controlled switches can control on and off of circuits of the fixed anode reflected ray tubes, so that control on raying is realized. The arc-shaped multi-focal point fixed anode gate controlled ray source is simple in structure and lower in cost, and can generate a ray of sufficient strength, and meanwhile, a sufficient number of focal points are distributed in the circumferential direction. The ray source can be applied to a static CT system.

The arc-shaped multi-focal point fixed anode gate controlled ray source provided in the invention is described above in detail. Any obvious modification made on the invention by a person of ordinary skill in the art without departing from the essential of the invention will constitute a patent infringement of the invention, and the person of ordinary skill in the art is to undertake corresponding legal liability.

What is claimed is:

1. An arc-shaped multi-focal point fixed anode gate controlled x-ray source, comprising an arc-shaped x-ray source housing, an x-ray tube bracket, a plurality of fixed anode reflected x-ray tubes and a plurality of gate controlled switches;
   wherein two ends of the respective fixed anode reflected x-ray tube are an anode end and a cathode end respectively, the anode end of the respective fixed anode reflected x-ray tube generates an x-ray beam by using a reflected fixed anode target, and a gate is arranged close to the cathode in the respective fixed anode reflected x-ray tube; the plurality of fixed anode reflected x-ray tubes are fixed on the arc-shaped x-ray source housing through the x-ray tube bracket, and focal points of the plurality of fixed anode reflected x-ray tubes are distributed on a distribution circle; and the plurality of gate controlled switches and the plurality of fixed anode reflected x-ray tubes are connected correspondingly.

2. The arc-shaped multi-focal point fixed anode gate controlled x-ray source according to claim 1, wherein
   the x-ray tube bracket is an arc-shaped bracket, the x-ray tube bracket is fixed on an inner arc wall plate of the arc-shaped x-ray source housing, the plurality of fixed anode reflected x-ray tubes are fixed on the x-ray tube bracket, and the focal points of the plurality of fixed anode reflected x-ray tubes are uniformly distributed on the distribution circle.

3. The arc-shaped multi-focal point fixed anode gate controlled x-ray source according to claim 1, wherein
   the x-ray tube bracket is uniformly provided with a plurality of through holes, anode ends of the plurality of fixed anode reflected x-ray tubes extend out of the through holes of the x-ray tube bracket respectively, and the plurality of fixed anode reflected x-ray tubes are fixed on the x-ray tube bracket through flanges respectively.

4. The arc-shaped multi-focal point fixed anode gate controlled x-ray source according to claim 1, wherein
   an inner arc wall plate and an outer arc wall plate of the arc-shaped x-ray source housing are respectively concentric to the distribution circle on which the focal points of the plurality of fixed anode reflected x-ray tubes are located; and
   wherein extension lines of a left side plate and a right side plate of the arc-shaped x-ray source housing pass through a center of the distribution circle on which the focal points of the plurality of the fixed anode reflected x-ray tubes are located.

5. The arc-shaped multi-focal point fixed anode gate controlled x-ray source according to claim 4, wherein
an included angle θ between an outer edge of the left side plate and an outer edge of the right side plate of the arc-shaped x-ray source housing equals 360°/N, and N is a positive integer greater than 1.

6. The arc-shaped multi-focal point fixed anode gate controlled x-ray source according to claim 5, wherein
the focal points of the plurality of fixed anode reflected x-ray tubes are uniformly distributed in an angle range α relative to the distribution circle, 180°>α>0°, and α is smaller than θ.

7. The arc-shaped multi-focal point fixed anode gate controlled x-ray source according to claim 6, wherein,
among n fixed anode reflected x-ray tubes provided within the arc-shaped x-ray source housing, an angle between two adjacent fixed anode reflected x-ray tubes is α/n, wherein n is a number of fixed anode reflected x-ray tubes provided within the arc-shaped x-ray source housing and n≥2.

8. The arc-shaped multi-focal point fixed anode gate controlled x-ray source according to claim 1, wherein
each of the fixed anode reflected x-ray tubes is provided with an independent gate controlled switch; and the respective gate controlled switch is fixed to a tube body of the respective fixed anode reflected x-ray tube through a bracket, and an output end of the gate controlled switch is connected to a gate of the respective fixed anode reflected x-ray tube through a wire.

9. An x-ray source, comprising a plurality of arc-shaped multi-focal point fixed anode gate controlled x-ray sources according to claim 1, wherein the plurality of arc-shaped multi-focal point fixed anode gate controlled x-ray sources are assembled into an integral ring structure, and focal points of all the fixed anode reflected x-ray tubes in the plurality of arc-shaped multi-focal point fixed anode gate controlled x-ray sources are circumferentially distributed on a distribution circle.

* * * * *